(12) United States Patent
Goodwin

(10) Patent No.: US 6,194,614 B1
(45) Date of Patent: Feb. 27, 2001

(54) PROCESS FOR THE PREPARATION OF BENZOTHIAZOLONE COMPOUNDS

(75) Inventor: Christopher Goodwin, Markfield (GB)

(73) Assignee: AstraZeneca UK Limited, London (GB)

(*) Notice: Subject to any disclaimer, the term of this patent is extended or adjusted under 35 U.S.C. 154(b) by 0 days.

(21) Appl. No.: 09/410,066

(22) Filed: Oct. 1, 1999

Related U.S. Application Data

(62) Division of application No. 09/029,831, filed on Mar. 10, 1998, now Pat. No. 6,087,508.

(30) Foreign Application Priority Data

Feb. 27, 1997 (SE) .................................................. 97000706
Feb. 17, 1998 (WO) ..................................... PCTSE9800274

(51) Int. Cl.⁷ ................................................. C07C 233/36
(52) U.S. Cl. ............................................................. 564/220
(58) Field of Search ............................................. 564/220

(56) References Cited

U.S. PATENT DOCUMENTS

| | | |
|---|---|---|
| 3,832,365 | 8/1974 | Wehrli . |
| 4,035,379 | 7/1977 | Fuchs . |
| 4,113,732 | 9/1978 | Opgenorth et al. . |
| 4,563,533 | 1/1986 | Rentél et al. . |
| 4,650,910 | 3/1987 | Henneke et al. . |
| 4,719,304 | 1/1988 | Rentél et al. . |
| 5,374,737 | 12/1994 | Dapperheld et al. . |
| 5,594,145 | 1/1997 | Forstinger et al. . |

FOREIGN PATENT DOCUMENTS

| | | |
|---|---|---|
| 1 472 849 | 5/1977 | (CH) . |
| 2631163 A1 | 1/1978 | (DE) . |
| 1 578 990 | 11/1980 | (DE) . |
| 3507824 A1 | 9/1986 | (DE) . |
| 3522941 A1 | 1/1987 | (DE) . |
| 0 102 -055 | 4/1984 | (EP) . |
| 0 529 600 A1 | 3/1993 | (EP) . |
| 0 622 362 A1 | 11/1994 | (EP) . |
| 2 298 548 | 8/1976 | (FR) . |
| 5-58998 * | 9/1993 | (JP) . |

OTHER PUBLICATIONS

Chemical Abstracts, vol. 59, p. 1963, "Preparation of tyrosol and 4–methoxyphenethyl alcohol," Yamada et al. Weinstock et al, "Synthesis and Evaluation of Non–Catechol D–1 and D–2 Dopamine Receptor Agonists: Benzimidazol–2–one . . . ," J. Med. Chem., vol. 30, pp. 1166–1176 (1987).

* cited by examiner

Primary Examiner—Robert Gerstl
(74) Attorney, Agent, or Firm—Nixon & Vanderhye

(57) ABSTRACT

There are described processes for the preparation of a compound of formula I

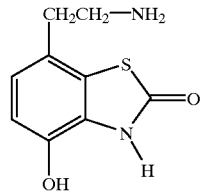

and novel intermediates in the preparative process.

1 Claim, No Drawings

PROCESS FOR THE PREPARATION OF BENZOTHIAZOLONE COMPOUNDS

This is a divisional of application Ser. No. 09/029,831, filed Mar. 10, 1998, now U.S. Pat. No. 6,087,508, the entire content of which is hereby incorporated by reference in this application.

The present invention relates to a process for the preparation of benzothiazolone compounds and to novel intermediates in the process of the invention. Benzothiazolone compounds are known. For example, WO 93/24473 describes 7-(2-aminoethyl)-benzothiazolone compounds of general formula

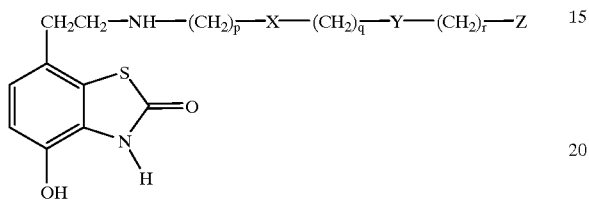

wherein
X and Y independently represent —S(O)$_n$— or —O—,
n represents 0, 1 or 2,
p, q and r independently represent 2 or 3,
Z represents phenyl optionally substituted by halogen, —OR$^1$, NO$_2$ or NR$^2$R$^3$; or a 5- or 6-membered N, O, or S containing heterocycle, and
R$^1$, R$^2$ and R$^3$ independently represent hydrogen or alkyl C$_{1-6}$,
and pharmaceutically acceptable derivatives thereof.

The compounds of WO 93/24473 may be prepared by any of several methods, for example by alkylation of the benzothiazolone compound of formula I

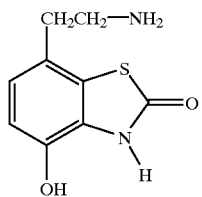

with an alkylating agent of formula

in which p, q, r, X, Y and Z are as defined above and L represents a leaving group, or alkylation of a compound of formula I, as defined above, with a compound of formula,

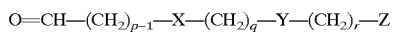

in which p, q, r, X, Y and Z are as defined above, in the presence of a reducing agent.

The present invention relates in particular to a novel process for the synthesis of compound I.

Routes for the synthesis of the compound are known, for example from Weinstock et al, *J. Med Chem.*, 1987, 30, 1166–1176.

According to the present invention, a process for the preparation of the compound of formula I

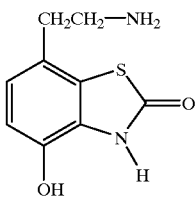

comprises converting the chlorobenzothiazole compound of formula II

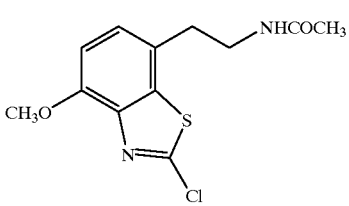

into the compound or formula I, for example using concentrated hydrobromic acid.

The compound of formula II is novel and may be prepared by halogenating the 2-aminobenzothiazole compound of formula III, for example using copper (II) chloride and copper (I) chloride and optionally ethanol, in HCl, e.g., 20% HCl to which is added sodium nitrite:

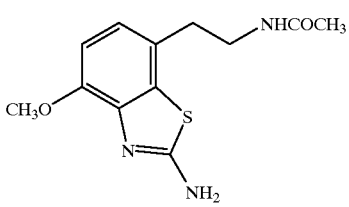

The compound of formula III is novel and may be prepared from a thiourea of formula IV,

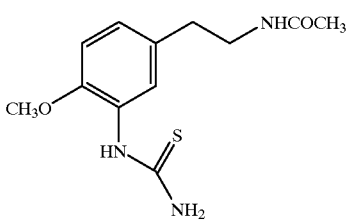

using a halogenating/oxidising agent, for example N-bromosuccinimide, bromine or N-chlorosuccinimide in an acidic solvent, e.g., a mixed acid solvent e.g. MeSO$_3$H/AcOH.

The compound of formula IV is novel and may be prepared by hydrolysis of a compound of formula V

V

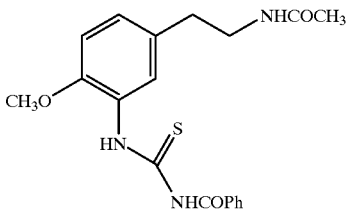

for example in water using a base such as K$_2$CO$_3$ or an alkali metal hydroxide, e.g. NaOH or KOH.

The compound of formula V is novel and may be prepared by reacting an aniline hydrochloride of formula VI

VI

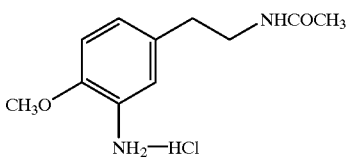

with benzoylisothiocyanate, for example in acetone or methylisobutylketone (MIBK).

The compound of formula VI is novel and may be prepared by hydrogenating a nitroacetamide of formula VII and treating with HCl

VII

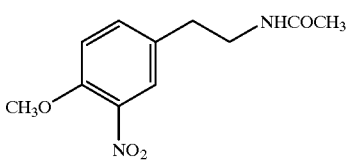

in any suitable solvent, for example in ethanol or 2-propanol, in the presence of palladium on charcoal.

The compound of formula VII is novel and may be prepared by nitrating an acetamide of formula VIII

VIII

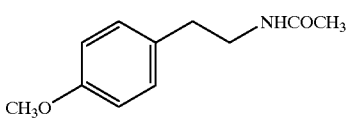

for example using HNO$_3$ in acetic acid.

The compound of formula VIII may be prepared from a compound of formula IX:

IX

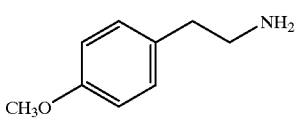

for example using acetic anhydride or acetyl chloride, either as solvent and reagent, or in the presence of dichloromethane and triethylamine.

In another aspect, the present invention provides a process for the preparation of compounds of formula I, comprising (i) converting a compound of formula IX into a compound of formula VIII, for example using acetic anhydride or acetyl chloride, either as solvent and reagent, or in the presence of dichloromethane and triethylamine, and (ii) converting the compound of formula VIII into the compound of formula I, for example by the stepwise preparation of compounds VII, VI, V, IV, III and II as described above.

The process of the present invention provides an easy process for the preparation of compound II, without the need to use undesirable starting materials, and giving the product compound in good yield.

The present invention also provides the novel compounds of formulae II, III, IV, V, VI and VII.

The following Example illustrates, but is not intended to limit, the invention.

a) Under an atmosphere of nitrogen, 2-(4-methoxyphenyl) ethylamine (100 g) was dissolved in dichloromethane. To this triethylamine (92.18 ml) was added and the resulting solution was cooled to 0° C. Acetic anhydride (62.40 ml) was added dropwise, over 35 mins, to the cold solution. A maximum exotherm of 6° C. was observed. The reaction mixture was stirred at room temperature for 40 mins. Tlc showed no trace of starting material on complete addition.

The reaction mixture was washed with dilute hydrochloric acid (2×1L) and saturated NaHCO$_3$ solution (2×1L) then dried over anhydrous MgSO$_4$, filtered and concentrated, in vacuo, to yield an off-white solid. This was dried, in vacuo, (T=40° C.).

b) A solution of 2-(4-methoxyphenyl)ethylacetamide (70 g) in glacial acetic acid (350 ml) was added, over 25 mins, to conc. nitric acid (339.6 ml) at 20° C. Cooling was applied so that the temperature was maintained between 18 and 20° C. The resulting solution was stirred at room temperature (24° C.) for 45 mins. Reaction progress was monitored by HPLC.

The reaction mixture was poured into iced water (2.7L) forming a precipitate/suspension. The product oiled out on stirring at room temperature. The mixture was extracted with dichloromethane (2×1L). A sample of the extract was washed with NaHCO$_3$ dried and concentrated for analysis. The extract was washed with saturated Na$_2$CO$_3$ solution (2×1L), causing the extract to become saturated with water. The extract was diluted slightly with dichloromethane (~100 ml), then dried over anhydrous MgSO$_4$, filtered and concentrated, in vacuo.

c) 2-(4-Methoxy-3-nitrophenyl)ethylacetamide (4.82 g) was dissolved in hot ethyl acetate (9.5 ml), then left to cool to room temperature. Cooling to 0° C. resulted in the formation of yellow crystals. These were filtered off, washed with cold ethyl acetate, and dried in vacuo (T=40° C.).

d) 2-(4-Methoxy-3-nitrophenyl)ethylacetamide (5.98 g) was dissolved in ethanol (150 ml), 10% palladium on charcoal (0.18 g) was added and the resulting mixture was hydrogenated at 3 bar, overnight.

The catalyst was filtered off and the filtrate concentrated to approximately one third of its volume. The solution was then gassed with hydrogen chloride until with cooling, a pale brown solid precipitated out. The mixture was allowed to stir overnight. The off-white solid was filtered off, washed with diethyl ether then dried, in vacuo, (T=50° C.).

e) The aniline hydrochloride (40.0 g) was dissolved in water (200 ml) and basified with aqueous sodium hydroxide solution (25% w/v) to pH≈11, extracted with dichloromethane (100 ml×3), dried (Na$_2$SO$_4$) and evaporated to dryness in vacuo to leave a pale pink solid. The solid was dissolved in acetone (140 ml).

Ammonium thiocyanate (12.35 g) was dissolved in acetone (AR grade, 120 ml) and benzoylchloride (17.3 ml) was added dropwise with stirring over 2 mins. The temperature rose from 22° C. to 38° C. over the addition and a white precipitate formed. The reaction was stirred at room temperature for a further 75 mins and then filtered, and washed with acetone (20 ml) to give a solution of benzoylisothiocyanate. This was added dropwise with stirring to the amine solution, over 40 mins. The temperature rose from 23° C. to 36° C. during the addition. A thick cream precipitate formed. The reaction was allowed to stir at room temperature for 16 hours and then the product was collected by filtration, washed with water (30 ml), sucked dry and then dried in vacuo at 60° C.

f) The N-benzoylthiourea (45.0 g) was suspended in water (330 ml). Sodium hydroxide solution (25 % w/v, 58 ml) was added and the stirred mixture heated to 75–80° C. for 20 minutes.

The mixture was cooled to room temperature with the aid of a cold water bath and then acidified to pH 7–8 using hydrochloric acid (~4N, 80 ml).

The mixture was cooled further in an ice bath—internal temp to 5° C., stirred cold for 15 mins and the product collected by filtration, washed with water (50 ml) and sucked dry. Dried in vacuo at 50° C.

g) Under an atmosphere of nitrogen, glacial acetic acid (112 ml) was added to methanesulfonic acid (823 ml). Cooling was required to keep the temperature below 30° C. The thiourea (93.5 g) was added to the resulting solution at 28° C. The resulting solution was cooled to 2° C. for the addition over 30 mins, of a solution of N-bromosuccinimide (59.14 g) in methanesulfonic acid (187 ml). The temperature was maintained between 2 and 5° C. The resulting solution was stirred at ~2° C. for 1 hour then allowed to stir at room temperature (max temp of 30° C. observed) for 22 hours. Reaction progress was monitored by HPLC. The reaction mixture was transferred to a dropping funnel then added, over 3.5 hours to a 25% solution of sodium hydroxide (4.675L) at 4° C. The temperature was maintained below 11° C. for the whole addition. An off-white solid precipitated from the reaction quench. The mixture was stirred between 7–10° C. for 1.25 hours then filtered. The solid was washed with water (2×200 ml), sucked dry, then dried in vacuo, (T=50° C.) to yield an off-white solid.

h) Under an atmosphere of nitrogen, 2-aminobenzothiazole (5 g) was dissolved in concentrated hydrochloride acid at 22° C. To this was added copper (II) chloride (1.26 g), copper(I) chloride (0.93 g) and ethanol (0.32 g). Complete dissolution of the aminobenzothiazole was observed. The solution was cooled to 15° C. for the gradual addition, over 1.75 hours, of an aqueous solution of sodium nitrite (3.9 g)—added below the surface of the reaction mixture via a syringe pump. The temperature was maintained between 13 and 18° C. $N_2$ evolution was observed. The reaction progress was monitored by HPLC. After 1.75 hours stirring at room temperature, the reaction mixture was quenched, over 5 mins, into stirred water at room temperature. A milky yellow solution was formed in which the product oiled out towards the end of the addition. The mixture was stirred for 60 hours. The solid was filtered off, washed with water (250 ml), air dried then dried, in vacuo (T=55 C), yielding on orange solid.

i) The chlorobenzothiazole (15.0 g) was suspended in concentrated hydrobromic acid (165 ml) under a nitrogen atmosphere and the mixture heated under reflux for 7.5 hours. The mixture was allowed to cool overnight and the precipitated product was collected by filtration, washed with isopropanol (20 ml) and sucked dry to give a yellow-brown powder which was dried in vacuo at 45° C.

j) The hydrobromide salt (13.3g) was suspended in water (130 ml) and warmed to 80–90° C. under a nitrogen atmosphere. Further water (20 ml) was added. Charcoal (1.1 g) was added and the solution/suspension stirred at ~70° C. for 15 minutes and then filtered hot to give a clear solution.

Concentrated hydrochloric acid (18 ml) was added to the filtrate and the mixture left to stir under nitrogen overnight. The solid was collected by filtration, washed with isopropanol (20 ml) and sucked dry to give a yellow powder, which was dried in vacuo at 45° C.

The product (5.0 g) was suspended in water (50 ml) under a nitrogen atmosphere and warmed to ~70° C. Charcoal (0.3 g) was added and the mixture stirred for 10 minutes and then filtered slowly to give a pale yellow solution. Concentrated hydrochloric acid (7 ml) was added and the mixture stirred and allowed to cool under nitrogen. The precipitated product was collected by filtration, washed with isopropanol (10 ml), sucked dry to give a pale yellow powder, and dried in vacuo at 45° C.

What is claimed is:

1. A compound of formula VI:

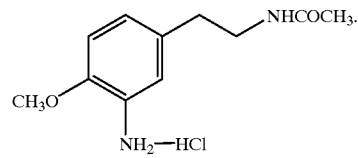

VI

* * * * *